United States Patent [19]
Meunier

[11] Patent Number: 5,783,826
[45] Date of Patent: Jul. 21, 1998

[54] METHOD AND APPARATUS FOR ANALYZING THE PHASES OF A MULTI-PHASE MIXTURE

[76] Inventor: Gerard Meunier, 5, Boulevard de la Mediterranee, 31400 Toulouse, France

[21] Appl. No.: 737,575

[22] PCT Filed: May 9, 1995

[86] PCT No.: PCT/FR95/00599

§ 371 Date: Nov. 15, 1996

§ 102(e) Date: Nov. 15, 1996

[87] PCT Pub. No.: WO95/31712

PCT Pub. Date: Nov. 23, 1995

[30] Foreign Application Priority Data

May 17, 1994 [FR] France ............... 94 06284

[51] Int. Cl.⁶ ........................................ G01J 3/06
[52] U.S. Cl. ........................... 250/341.8; 250/341.1
[58] Field of Search .................... 250/341.1, 341.8, 250/339.11

[56] References Cited

U.S. PATENT DOCUMENTS

| | | | |
|---|---|---|---|
| 4,099,871 | 7/1978 | Sunahara et al. | 356/73 |
| 4,975,581 | 12/1990 | Robinson | 250/339.11 |

*Primary Examiner*—Don Wong

[57] ABSTRACT

An apparatus and method of analyzing phases of a multiphase mixture allows an analysis of a mixture that has great turbidity or is opaque. An emission device emits electromagnetic radiation in a direction of a measurement cell. The electromagnetic radiation is back scattered by the mixture and is detected by a primary detection device. A secondary detection device may detect electromagnetic radiation that is transmitted but is not back scattered by the mixture. A moving device displaces the primary detection device in order to carry out a plurality of detections at a predetermined step over the length of the measurement cell. The scanning of the cell allows one to obtain a cycle of measurements that produces a phase profile of the mixture.

23 Claims, 5 Drawing Sheets

METHOD AND APPARATUS FOR ANALYZING THE PHASES OF A MULTI-PHASE MIXTURE

BACKGROUND OF THE INVENTION

1. Field of the Invention

This invention pertains to methods and instruments used for analysis of the phases of a multi-phase mixture, that allow in particular the detection and measurement as a function of time of nascent destabilization or demixtion phenomena in the mixture, these phenomena being sedimentations, of emulsions or suspensions for example. In particular, the areas of application of the invention include the chemical and para-chemical industries, and more broadly in the areas for which it is necessary to analyze the structure as well as the stability of a multi-phase mixture or to determine the structure of a mixture.

2. Description of Related Art

The prior art discusses a device used for the determination of the number of phases of a partially liquid mixture. This device includes a vertical parallelepiped cell in which one places the mixture and subjects it to optical radiation. An optical sensor that is placed opposite the optical transmitter allows one to detect the radiation transmitted by the mixture. The movement of the transmitter and the sensor along the height of the cell allows one to count the phases present in the mixture by the measurement variations of the optical transmission in each phase and at the interface of the phases.

Such a device, which uses only optical transmission through the mixture, allows applications that are limited to transparent mixtures or mixtures having only slight turbidity. It also allows analyses that only determine the number of phases of the mixture. In addition, the use of a parallelepiped cell does not allow good filling for a highly viscous mixture, and it does not allow good homogeneity of the mixture through intermingling.

The prior art also discusses a device that allows one to partially overcome these disadvantages. This device utilizes a sensor of the radiation which is diffused by the mixture and thereby allows one to determine, because of the turbidity differences of the mixture, different phases that are contained in the latter.

This device only allows applications to mixtures having average turbidity. This is the reason for the principle of detecting diffused radiation that requires a certain transparency of the mixture. Therefore, this device does not allow one to study opaque or highly turbid mixtures.

SUMMARY OF THE INVENTION

The present invention essentially allows one to overcome these disadvantages. More particularly, it consists of a method of analyzing phases of a multi-phase mixture containing at least the following stages:

placing the mixture in a tubular measurement cell with cylindrical cross section;

to transmit electromagnetic radiation in the direction of the measurement cell, characterized in that the method consists in:

detecting electromagnetic radiation which is back scattered by the mixture in a plane perpendicular to the longitudinal axis of the tubular measurement cell, the longitudinal axis being arranged vertically, and the measurement cell being transparent;

to carry out a plurality of detections of the back scattered electromagnetic radiation, according to a predetermined step on the total length of the longitudinal axis of the said tubular measurement cell, the said number of detections constituting a measurement cycle of the said mixture.

The method in accordance with the invention allows an analysis of a mixture that has great turbidity or is opaque, dividing the mixture up into measurement sections which are perpendicular to the longitudinal axis of the cell, by means of detection by back scattering of the electromagnetic radiation, while allowing one to obtain a homogeneous mixture in the cell at the time of mixing through the intermediary of the use of a measurement cell which houses a mixture in a tubular part of the cylindrical section of the cell, preferably a part with circular cross section. The scanning of the cell through determinations which are made at a predetermined rate allows one to thereby obtain a cycle of measurements that produces a phase profile of the mixture. A narrow scan, preferably less than or equal to the thickness of the plane of detection, allows in particular, one to detect nascent phenomena in the mixture as a demirtion coalescence, or a flocculation phenomena, at any place of the mixture.

According to one characteristic advantage, the method in accordance with a preferred embodiment the invention consists in:

detecting the electromagnetic radiation transmitted by the mixture in the plane which is perpendicular to the longitudinal axis of the tubular measurement cell;

to carry out a plurality of detections of the transmitted electromagnetic radiation according to the step, the plurality of detections of the transmitted electromagnetic radiation being included in the measurement cycle of the mixture.

This characteristic allows the analysis of a slightly turbid or transparent mixture, and in cooperation with the detection of electromagnetic radiation which is back scattered by the mixture, it brings about the opportunity of analyzing all kinds of multi-phase, transparent, turbid, and opaque mixtures.

According to another advantageous embodiment, the plane of detection has a thickness between 30 and 50 micrometers.

This embodiment allows precise resolution of the measurement, that in particular allows detection of nascent phenomena in mixture as demixtion, sedimentation, coalescence, or creaming phenomena. This is a particularly interesting characteristic for the study of stability over time of a mixture without having to wait for the complete appearance of the phenomenon that can be quite long.

According to another advantageous embodiment, the back scattered electromagnetic radiation is detected at an angle between 90° and 180° with respect to the direction of emission of the electromagnetic radiation.

This embodiment allows optimal detection of the electromagnetic radiation that is back scattered by a mixture having great opacity, especially in the vicinity of the cell-mixture curve interface.

According to yet another advantageous embodiment, the method according to the invention detects the electromagnetic radiation that is back scattered at a point of the cell-mixture interface.

This embodiment allows the analysis of a highly turbid mixture, the back scattered rays do not have to penetrate deeply into the mixture in order to be detected during back scattering.

According to still another advantageous embodiment, the method in accordance with the invention repeats the measurement cycle at a predetermined time interval.

This embodiment allows one to obtain phase profiles of a mixture at different moments. This allows the study of stability or evolution of the mixture as a function of time.

According to even another advantageous embodiment, the method in accordance with the invention inputs at least one of the measurement cycles. Other advantageous embodiments include processing and comparing the measurement cycles in order to understand the evolution of phases in the mixture between the measurement cycles.

These characteristics allow one to obtain a kinetic picture of the mixture, the processing of the measurement cycles allows one essentially to make two phase profiles of the mixture comparable, which are separated by correcting, in particular, the dehydration of the mixture in the course of time.

The invention also has as an object an apparatus for analyzing the phases of at least one multi-phase mixture that allows one to implement a method in accordance with the invention for analyzing phases of a multi-phase mixture.

The invention will be better understood, and other advantages and characteristics will be apparent, from reading the description of one example of a mode of implementation of the apparatus in accordance with the invention for analyzing phases of the multi-phase mixture. Also, the preferred embodiments will be apparent by looking at a few of the following application examples that are accompanied by the attached drawings. These examples are given by way of illustration without thereby implying any restrictive interpretation of the invention.

DETAILED DESCRIPTION OF THE INVENTION

Figure 1:
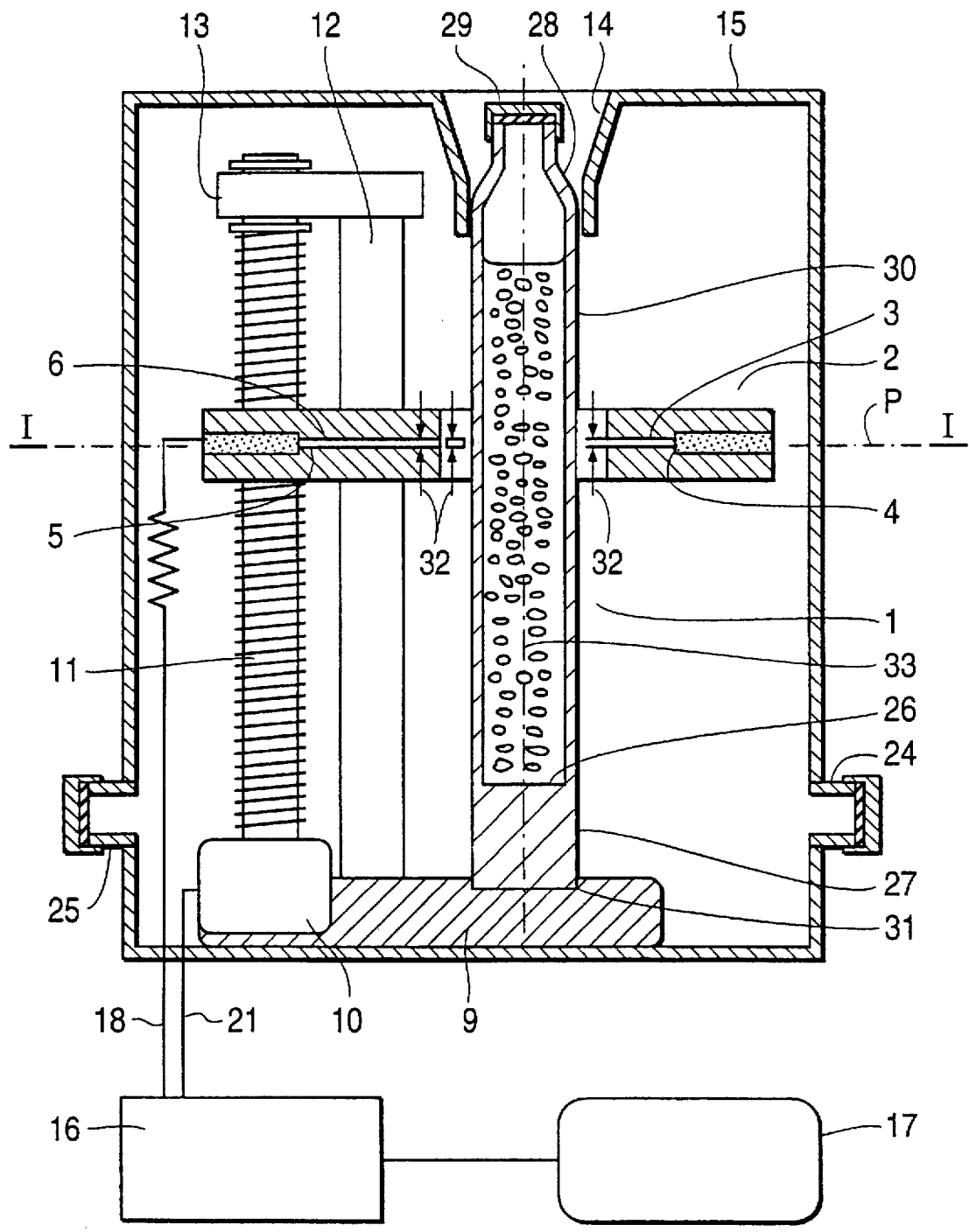
FIG. 1 represents one mode of implementation of an apparatus in accordance with the invention shown in partial frontal view.

The apparatus shown in FIG. 1 includes a measurement cell 1 which contains a multi-phase mixture that is to be analyzed. The cell 1 has an upper part 28 which is open in order to permit filling of the cell 1. The upper part 28 is closed by a stopper 29 which is preferably of the screw type. The upper part 28 can, in particular, be provided with an attachment (not shown) that is capable of working with a centrifuge device.

The cell 1 advantageously has an lower part 27 with a flat and horizontal base section 26 so that the base part 26 be included in a measurement plane, as will be explained subsequently. The lower part 27 is of a height that allows one to free it from the mobile support 2 beneath the bottom section 26 in order to ensure complete scanning of the mixture. The upper 28 and lower 27 parts are connected by an intermediate tubular part 30 of circular cross section which houses the mixture, the latter being therefore present in measurement cell 1 preferably in the shape of a vertically straight cylinder with circular cross section.

Cell 1 is vertically placed in the apparatus, preferably positioned in vertical support in a housing 31 within a base 9, and arranged in lateral support in an opening 14 of the cell entry. The opening 14 has a shape complementary to that of cell 1 and is adjusted to the cell 1. The opening 14 is supported by a surrounding wall 15 that will subsequently be described.

One should note that cell 1 can alternatively be positioned in vertical support on opening 14 of the enclosing wall 15 by the intermediary of the upper part 28 in any known manner. In this case (not shown), the lower part 27 of cell 1 is not in contact with the support 9, the space between the lower part 27 and the support 9 being used principally for separation from the mobile support 2 beneath bottom section 26 in order to ensure complete scanning of the mixture.

The intermediate part 30 at least of cell 1 is made, for example, of glass or transparent plastic materials in order to ensure transmission of the electromagnetic radiation.

The apparatus shown in FIG. 1 includes a mobile support 2 which carries an emission of electromagnetic radiation in the direction of the measurement cell, a detection device in order to detect electromagnetic radiation that is back scattered by the mixture, and preferably another of detection device in order to detect electromagnetic radiation transmitted by the mixture.

Figure 2:
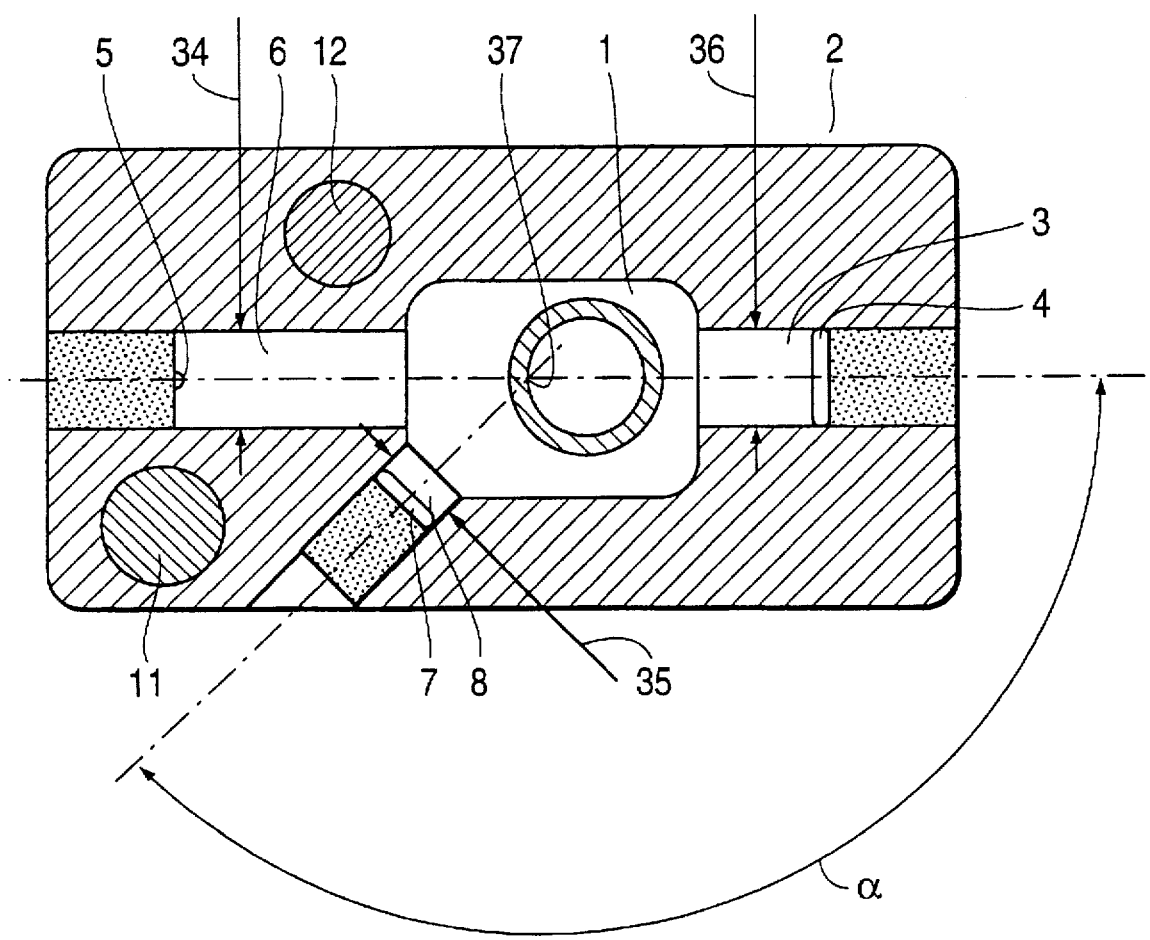
FIG. 2 presents a partial section along line I—I of FIG. 1.

As shown in FIGS. 1 and 2 the mobile support 2 surrounds measurement cell 1 and supports the emission of electromagnetic radiation. The mobile support 2 preferably the at least one electroluminescent diode 5 (LED) which emits in the near infrared, and more particularly in a wavelength of about 860 nanometers. The radiation emitted by diode 5 passes through a horizontal straight slit 6 having a preferred width 32 between about 30 and 50 micrometers, and preferably equal to about 40 micrometers. It is positioned in such a manner that it will permit irradiation of the mixture along a plane P, with a thickness between about 30 and 50 micrometers, and preferably equal to about 40 micrometers, which is perpendicular to the longitudinal axis 33 of the intermediate part 30 of the measurement cell 1. An important characteristic of the plane P of irradiation is that it would be parallel, if necessary, to the free surface of the mixture contained in the cell 1.

The electromagnetic radiation that is back scattered by the mixture is sensed by detection devices, including at least one photodiode 7, at an angle α which is between about 90° and 180°, preferably equal to 135° with respect to the direction of emission of the electromagnetic radiation as shown in FIG. 2. The back scattered electromagnetic radiation is sensed by the photodiode 7 after having passed through a back scattering slit 8 which is preferably having a width 32 between about 30 and 50 micrometers, and preferably equal to about 40 micrometers. The slit 8 is arranged in the same plane as the emission slit 6.

The electromagnetic radiation transmitted by the mixture is sensed by detection equipment, including at least one photodiode 4, directly opposite the direction of emission of the electromagnetic radiation as shown in FIG. 2. The transmitted electromagnetic radiation is detected by the photodiode 4 after having passed through a horizontal rectilinear slit 3 preferably having a width 32 between about 30 and 50 micrometers, and preferably equal to about 40 micrometers. The slit 3 is located in the same plane as the emission slit 6.

The length 34 of the emission slit 6 will preferably be around 40% of the diameter of the intermediate part 30 of the cell 1 and symmetrical with the cell 1, and the length 36 of the transmission slit 3 will preferably be around 50% of the diameter of the intermediate part 30 of cell 1.

The length 35 of the back scattering slit 8 will be determined as a function of the angle α in such a manner that it can pick up the maximum amount of back-scattered radiation. The longitudinal axis of the back scattering slit 8 will preferably be secant with the longitudinal axis of emission slit 6 at a point 37 of the cell-mixture interface as shown in FIG. 2.

The apparatus shown in FIG. 1 will include a displacement of the mobile support 2 parallel to the longitudinal axis 33 of the intermediate part 30 of cell 1. The displacement will include, for example, a step motor 10 secured in base 9 that controls rotation of a vertical screw 11 passing through the mobile support 2. The screw 11 will transfer the mobile support 2 which is locked in rotation on a column 12. The rotation step of motor 10 and the pitch of the screw will be selected in such a manner as to allow maximum displacement pitch of the mobile support 2 being transferred that is less than or equal to the width 32 of the slits 3, 8. A connecting piece 13 will connect the screw 11 and the column 12 at the top in order to improve rigidity of the unit and to ensure rotation and guidance of screw 11.

Preferably, the vertical path of the mobile support 2 must allow one to scan the entire height of the intermediate part 30 of cell 1 which contains the mixture being investigated. To achieve this, the measurement plane that contains slits 3, 6, and 8 must be able to scan the bottom part 26 of the cell and the upper surface of the mixture, for example. The free surface of the latter is shown in FIG. 1. One should note that one can envision the use of a cell whose lower part is hemispherical, according to the desired analysis, and in this case the measurement plane can reach the lower part of the mixture if desired.

The apparatus shown in FIG. 1 includes a surrounding wall 15 enclosing at least cell 1 and mobile support 2 and preferably the base 9 and displacement device for mobile support 2. The surrounding wall 15 is preferably thermally insulated and will include connections 24 and 25 for fluid circulation channels (not shown) established by thermal regulation (not shown) to control the temperature inside surrounding wall 15. For this purpose, the surrounding wall 15 can include any known type of temperature sensor (not shown here). The surrounding wall 15 has in its upper part an opening 14 for the introduction of cell 1 inside the opening 14 as has already been described in detail. The opening 14, as well as the cell 1, preferably allows for positioning a replacement of cell 1 in the surrounding wall 15 in an angular position identical to a preceding position. This positioning can, for example, be comprised of a mark on cell 1 opposite a mark on opening 14 or a lug or notch system (not shown here).

The emitting diode(s) 5, the photodiodes which detect back scattered and transmitted radiation, 7 and 4 respectively, the mobile support 2 displacement motor 10, the temperature sensor and the thermal regulating devices if necessary (not shown), are connected to electronic devices 16 for control and measurement through cables 18, the electronic devices 16 being preferably connected to computer devices 17 used as an interface between the apparatus in accordance with the invention and a user.

The electronic devices 16 allow one to control motor 10 for successive displacements of mobile support 2 and, to control emission of diode 5, to carry out a detection of back scattered and transmitted radiation for each displacement. Thus, a user can to measure the quantity of back scattered radiation and the quantity of transmitted radiation respectively by the mixture in comparison with the quantity of back scattered radiation and the quantity of transmitted radiation by respective standard control devices in order to obtain a cycle of mixture measurements in cell 1.

The reference standard device (not shown here) is preferably internal to the apparatus in accordance with the invention and can, for example, be the air for transmitted radiation and an opaque reference placed in the lower part 27 or upper part 28 of cell 1, or on support 9 for back-scattered radiation.

The computer devices 17 can be a microprocessor which preferably includes devices for storing measurement cycles transmitted by the measurement electronics, time measurement devices in order to carry out several measurement cycles at different times, and software packages which allow transmission of a large number of instructions provided by a user, to the control electronic device. The software packages can also provide processing of the measurement cycles for their analytical interpretation. The computer devices 17 preferably include a monitor and/or a printer (not shown here) which allow visualization of the measurements, especially in graphic form, as will be developed subsequently with the description of FIGS. 3, 4, and 5.

Figure 3:
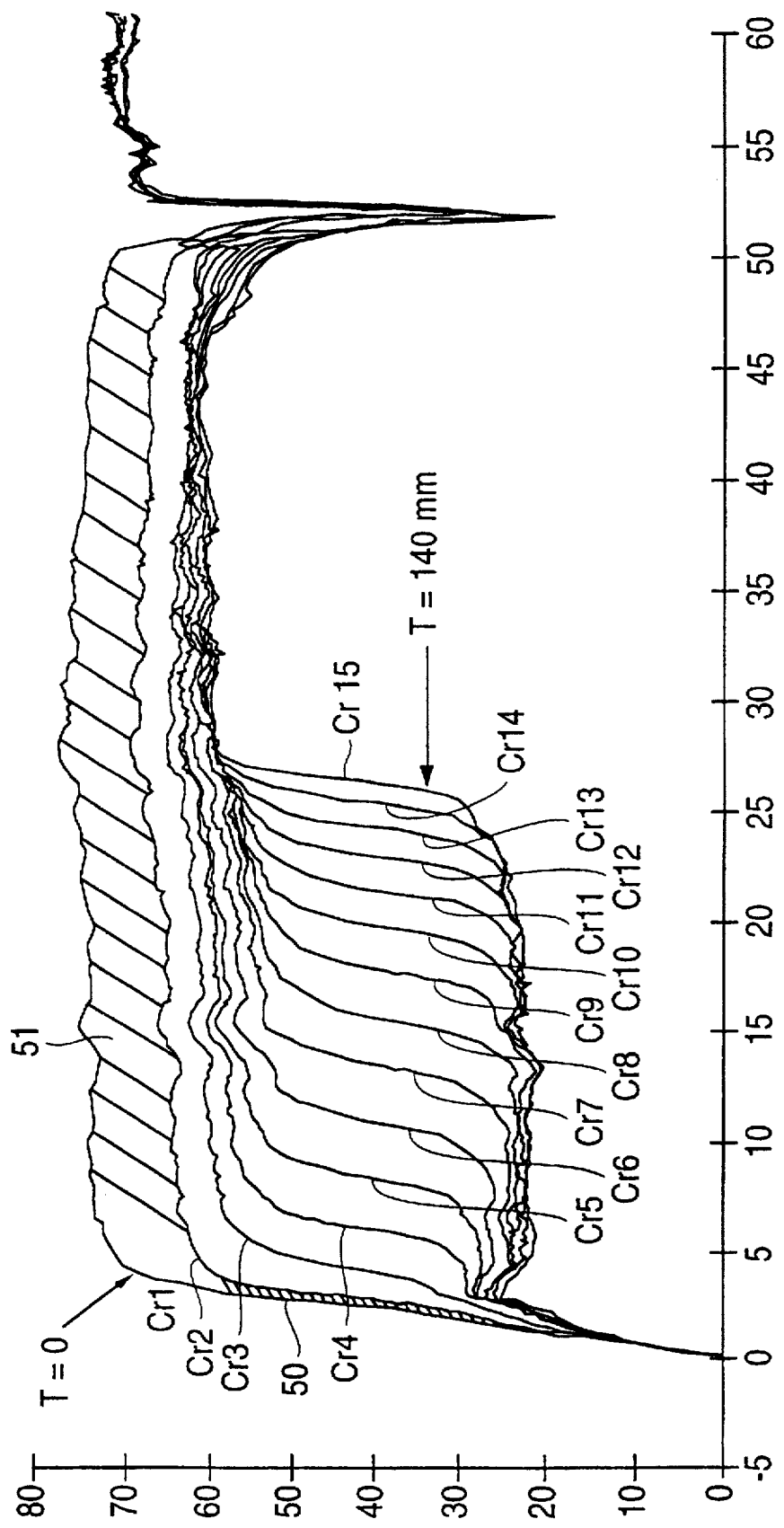
FIG. 3 gives an example of implementation of the apparatus in accordance with the invention showing a large number of measurement cycles in a mixture taken at different intervals.

FIG. 3 presents an analysis diagram of phases of a mixture which includes 45% oil and 55% water obtained with an embodiment in accordance with the invention and includes a measurement cell with a flat base arranged vertically. The mixture represents a free surface in the upper part of the measurement cell. The mixture was shaken at a time T=0 and is present in the form of a highly turbid emulsion. The curve $Cr_1$–$Cr_{15}$ of back scattering illustrates several measurement cycles at a mixture height of 60 mm at different times from the time T=0 for $Cr_1$ at the time T=140 mm for $Cr_{15}$, as FIG. 3 shows. Each curve is comprised of 1500 detections at a rate of one detection every 40 micrometers. The time interval between two measurement cycles is regular and equal to 10 min starting at instant T=0, and the time necessary for a measurement cycle is approximately 5 seconds. The straight line of the abscissa is graduated in mm representing the unit of height of the mixture and the line of the ordinate is calibrated in % representing the quantity of radiation back scattered by the mixture with respect to the quantity of radiation back scattered by an internal reference element.

In FIG. 3 the hatched line area 50 between curves $Cr_1$ and $Cr_2$ illustrates a nascent phenomenon of a separation into two emulsions of different particular size and concentration, and the hatched line area 51 between curves $Cr_1$ and $Cr_2$ represents a nascent phenomenon, already at an advanced stage, a coalescence in the mixture.

Figure 4:
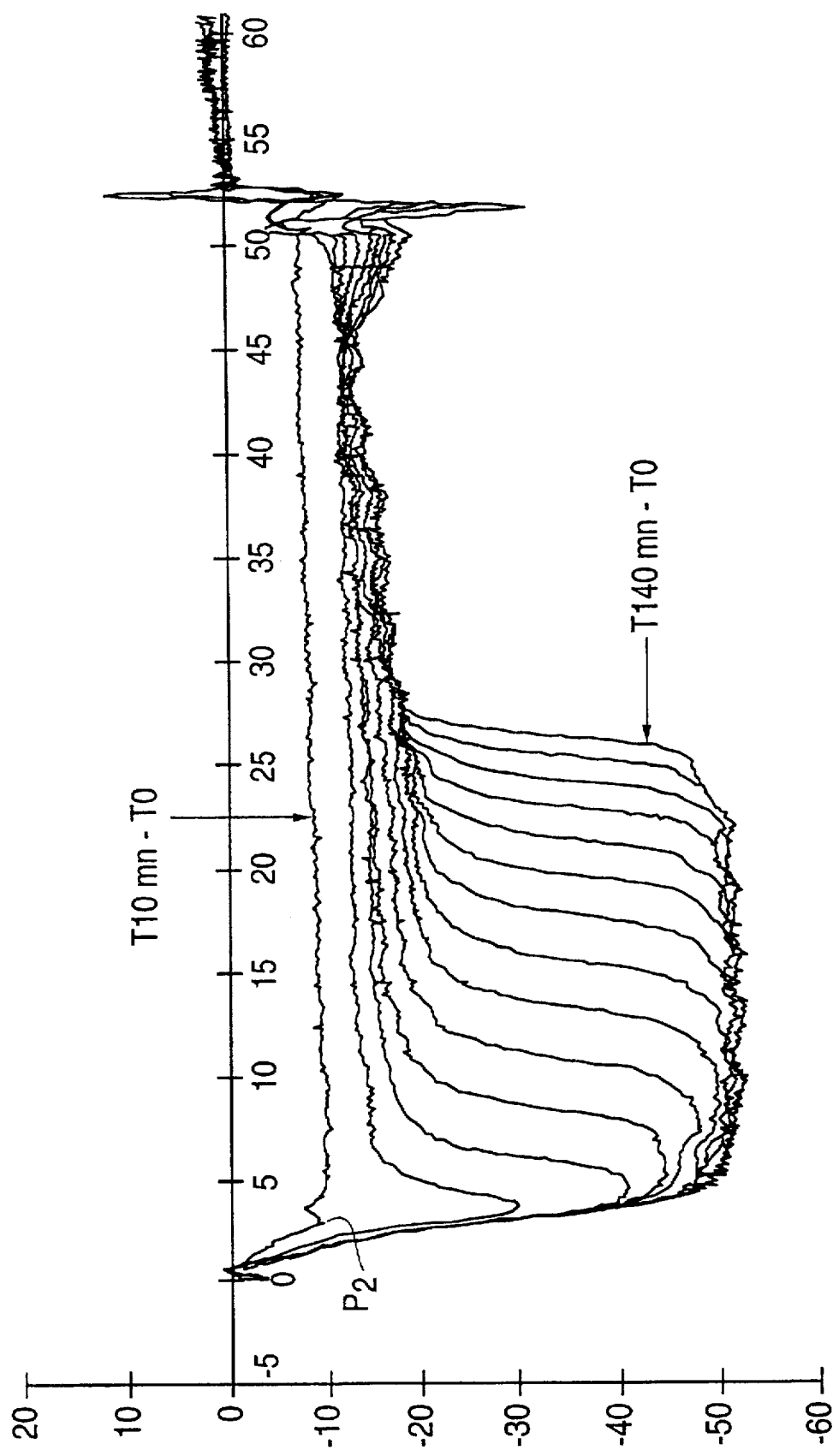
FIG. 4 gives an example analysis of the measurement cycles of FIG. 3.

FIG. 4 gives an example of processing of the measurement cycles of FIG. 3, from which we have withdrawn, detection by detection for each curve $Cr_2$–$Cr_{15}$, respectively the value of the curve $Cr_1$ at the instant T=0, thereby developing the analysis of the evolution of the mixture in the course of successive measurement cycles. For example, in FIG. 4 the curve referenced as T10 min-T0 is equal to the curve $Cr_2$ (at the instant T=10 min) minus the curve $Cr_1$ (at the instant T=0) in FIG. 3.

FIG. 4 particularly emphasizes, by the peak $P_2$ which arises from this processing, the appearance of the phenomenon which gives rise to the separation which was already mentioned.

Figure 5:
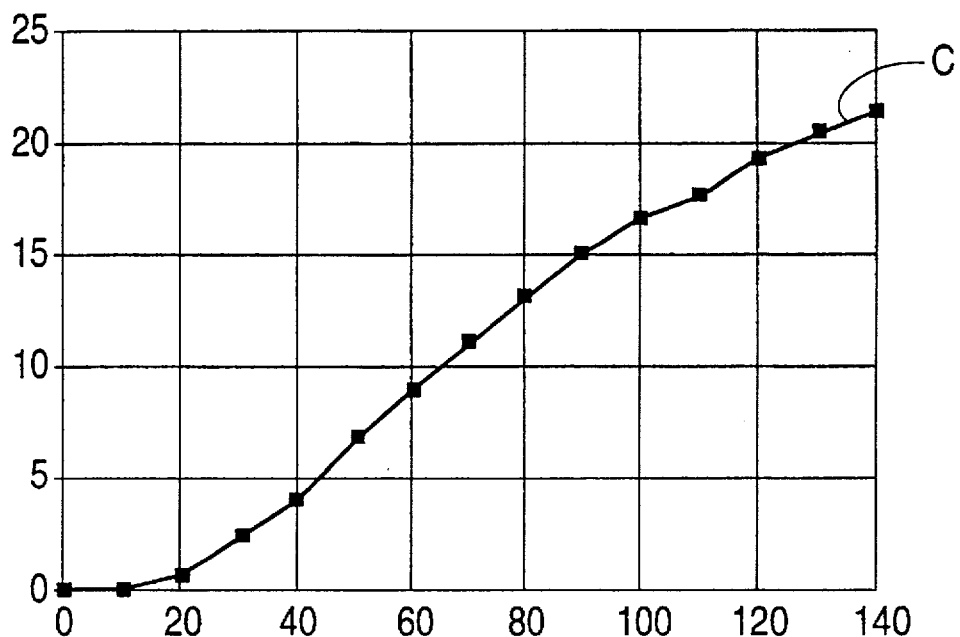
FIG. 5 presents a comparison of the processed measurement cycles of FIG. 4 and gives the evolution of phases in a mixture over the course of time.

FIG. 5 gives a comparison of the measurement cycles analyzed in FIG. 4, in which each point of the curve C illustrates the variation of the quantity of back scattered radiation caused by a separation in the mixture related to the quantity of radiation back scattered by the mixture at the instant T=0 as a function of time. The abscissa is graduated in min and the ordinate is graduated in %. Each respective point of the curve C is deducted from a respective curve of FIG. 4 by integration of the respective separation peaks of each curve. The curve C shows the kinetic aspects of the mixture separation.

Figure 6:
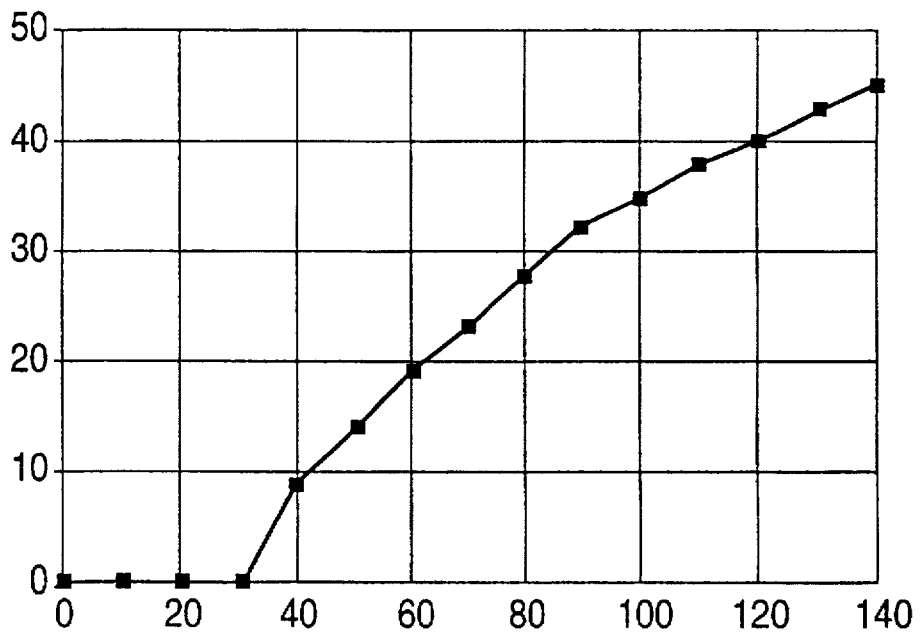
FIG. 6 compares the visual perception of the evolution of phases shown in FIG. 5.

One will note the speed and precision with which it is possible to detect the phenomenon which gives rise to creaming, the curve C of FIG. 5 causing appearance of this phenomenon at the end of only a few minutes, relative to the curve of FIG. 6 which has been established as a function of the visual evaluations of the phenomenon by a user. One should note that for FIG. 6 the ordinate line is graduated in % of the mixture height.

I claim:

1. A method of analyzing phases of a multi-phase mixture, which includes at least the following stages:
   placing the mixture in a tubular measurement cell with cylindrical cross section;
   emitting an electromagnetic radiation in a direction of the measurement cell;
   detecting the electromagnetic radiation which is back scattered by the mixture in a plane which is substantially perpendicular to a longitudinal axis of the tubular measurement cell, said longitudinal axis arranged substantially vertically, and the measurement cell being substantially transparent;
   carrying out a plurality of detections of the back scattered electromagnetic radiation at a predetermined step on the total length of the longitudinal axis of the tubular measurement cell, the plurality of detections providing a measurement cycle of the mixture.

2. The method according to claim 1 further comprising:
   detecting the electromagnetic radiation transmitted by the mixture in the plane which is substantially perpendicular to the longitudinal axis of the said tubular measurement cell;
   carrying out a plurality of detections of the transmitted electromagnetic radiation according to the step, the plurality of detections of the transmitted electromagnetic radiation being included in the measurement cycle of the mixture.

3. The method according to claim 1 wherein the plane has a thickness between about 30 and 50 micrometers.

4. The method according to claim 1 wherein the back-scattered electromagnetic radiation is detected at an angle between about 90° and 180° with respect to the direction of emission of the electromagnetic radiation.

5. The method according to claim 4 wherein the angle is equal to about 135°.

6. The method according to claim 1 wherein the back-scattered electromagnetic radiation is detected at a point of the cell-mixture interface.

7. The method according to claim 2 wherein the transmitted electromagnetic radiation is detected facing the direction of emission of the electromagnetic radiation.

8. The method according to claim 1 further comprising providing another measurement cycle at a predetermined time interval.

9. The method according to claim 8, further comprising at least one of the measurement cycle and the another measurement cycle.

10. The method according to claim 9 further comprising:
    analyzing the measurement cycles, and
    comparing the measurement cycle and the another measurement cycle to determine an evolution of the phases in the mixture between the measurement cycles.

11. An apparatus for analyzing phases of at least one multi-phase mixture, comprising:
    a tubular measurement cell with a cylindrical cross section to house the mixture;
    an emitting device that emits electromagnetic radiation in a direction of the measurement cell;
    a primary detection device that detects electromagnetic radiation back scattered by the mixture in a plane substantially perpendicular to a longitudinal axis of the tubular measurement cell, the longitudinal axis being arranged substantially vertically and the measurement cell being substantially transparent; and
    a moving device that displaces the primary detection device in order to carry out a plurality of detections at a predetermined step over a total length of the longitudinal axis of the tubular measurement cell, the plurality of detections providing a measurement cycle of the mixture.

12. The apparatus according to claim 11 wherein the measurement cell includes a tubular part with a circular cross section that houses the mixture.

13. The apparatus according to claim 11 further comprising a secondary detection device that detects electromagnetic radiation transmitted by the mixture in the plane which is substantially perpendicular to the longitudinal axis of the tubular measurement cell, the moving device displacing the secondary detection device in order to carry out a plurality of detections of the transmitted electromagnetic radiation at the predetermined step, the plurality of detections of the transmitted electromagnetic radiation being included in the measurement cycle of the mixture.

14. The apparatus according to claim 11 wherein the primary detection device, includes a primary rectilinear slit included in the plane.

15. The apparatus according to claim 14 wherein the primary rectilinear slit has a width between about 30 and 50 micrometers.

16. The apparatus according to claim 14 wherein the primary detection device is placed at an angle between about 90° and 180° with respect to the direction of emission of the electromagnetic radiation.

17. The apparatus according to claim 16 wherein the angle is equal to about 135°.

18. The apparatus according to claim 14 wherein the emitting device includes another rectilinear slit having a longitudinal axis substantially secant with a longitudinal axis of the primary rectilinear slit at a point of a cell-mixture interface.

19. The apparatus according to claim 13 wherein the secondary detection device is placed substantially in the direction of emission of the electromagnetic radiation.

20. The apparatus according to claim 11 a measuring device that measures an increment of time in order to provide another measurement cycle at a predetermined time interval.

21. The apparatus according to claim 20 further comprising a memory device that stores at least one of the measurement cycle and the another measurement cycle.

22. The apparatus according to claim 21 further including a processing device for processing at least one of the measurement cycles, and an analyzer that compares the measurement cycles in order to determine an evolution of the phases in the mixture between the measurement cycles.

23. An apparatus for analyzing phases of at least one multi-phase mixture, comprising:

a tubular measurement cell with a cylindrical cross section to house the mixture;

emission means for emitting electromagnetic radiation in a direction of the measurement cell primary means for detecting electromagnetic radiation back scattered by the mixture in a plane substantially perpendicular to a longitudinal axis of the tubular measurement cell, the longitudinal axis being arranged substantially vertically and the measurement cell being substantially transparent; and moving means for displacing the primary detection device in order to carry out a plurality of detections at a predetermined step over a total length of the longitudinal axis of the tubular measurement cell, the plurality of detections providing a measurement cycle of the mixture.

* * * * *